United States Patent
Edelhauser et al.

(10) Patent No.: US 12,220,153 B2
(45) Date of Patent: *Feb. 11, 2025

(54) RING HOLE PLANNING FOR EXTERNAL FIXATION FRAMES

(71) Applicant: Stryker European Operations Holdings LLC, Kalamazoo, MI (US)

(72) Inventors: Adam John Edelhauser, Nyack, NY (US); Ashish Gangwar, Gurgaon (IN); Sridhar Anjanappa, Gurgaon (IN); Subash K. Mannanal, Mahwah, NJ (US); Patrick Valli, Brookside, NJ (US)

(73) Assignee: Stryker European Operations Holdings LLC, Portage, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/455,681

(22) Filed: Aug. 25, 2023

(65) Prior Publication Data

US 2023/0397934 A1   Dec. 14, 2023

Related U.S. Application Data

(63) Continuation of application No. 17/383,585, filed on Jul. 23, 2021, now Pat. No. 11,771,466, which is a
(Continued)

(51) Int. Cl.
*A61B 17/62* (2006.01)
*A61B 17/56* (2006.01)
*A61B 34/10* (2016.01)

(52) U.S. Cl.
CPC .............. *A61B 17/62* (2013.01); *A61B 34/10* (2016.02); *A61B 2017/564* (2013.01); *A61B 2034/102* (2016.02); *A61B 2034/104* (2016.02)

(58) Field of Classification Search
CPC ..... A61B 17/66; A61B 17/62; A61B 17/6466; A61B 17/6416; A61B 17/645;
(Continued)

(56) References Cited

U.S. PATENT DOCUMENTS

| 5,540,686 A | 7/1996 | Zippel |
| 5,546,942 A | 8/1996 | Zhang |

(Continued)

FOREIGN PATENT DOCUMENTS

| DE | 102006048451 A1 | 4/2008 |
| RU | 2448663 C1 | 4/2012 |

(Continued)

OTHER PUBLICATIONS

Craveiro-Lopes, MD, Software Assisted "Ortho-SUV Frame", Int'l Congress on External Fixation & Bone Reconstruction, Oct. 22, 2010.
(Continued)

*Primary Examiner* — Eduardo C Robert
*Assistant Examiner* — Tara Rose E Carter
(74) *Attorney, Agent, or Firm* — SLEMAN & LUND LLP

(57) ABSTRACT

An external fixation system includes first and second fixation members having first and second pluralities of mounting holes, respectively. The first and second plurality of holes are configured to receive first and second ends of a plurality of struts, each strut having a default or initial mounting position. A simulation of the correction may be performed with the struts in the default positions, but it may be determined that the correction is not achievable. Additional simulations of the correction may be performed with the ends of the struts in different mounting positions to determine if other mounting positions of the struts allow the correction to be completed. During the correction, if one of
(Continued)

the struts reaches a maximum length, it may be disconnected and reconnected to a different mounting hole so that, after being reconnected, the strut may be further increased in length to continue the correction.

20 Claims, 10 Drawing Sheets

Related U.S. Application Data continuation of application No. 15/948,055, filed on Apr. 9, 2018, now Pat. No. 11,083,495, which is a continuation of application No. 15/133,649, filed on Apr. 20, 2016, now Pat. No. 10,010,346.

(58) Field of Classification Search
CPC . A61B 17/6458; A61B 17/60; A61B 17/6425; A61B 17/6441; A61B 17/6475
USPC .................................................... 606/53–59
See application file for complete search history.

(56) References Cited

U.S. PATENT DOCUMENTS

| | | |
|---|---|---|
| 5,681,309 A | 10/1997 | Ross, Jr. |
| 5,702,389 A | 12/1997 | Taylor |
| 5,728,095 A | 3/1998 | Taylor |
| 5,824,085 A | 10/1998 | Sahay |
| 5,880,976 A | 3/1999 | DiGioia, III |
| 5,891,143 A | 4/1999 | Taylor |
| 5,971,984 A | 10/1999 | Taylor |
| 6,030,386 A | 2/2000 | Taylor |
| 6,129,727 A | 10/2000 | Austin |
| 6,205,411 B1 | 3/2001 | DiGioia, III |
| 6,701,174 B1 | 3/2004 | Krause |
| 6,711,432 B1 | 3/2004 | Krause |
| 7,039,225 B2 | 5/2006 | Tanaka |
| 7,280,683 B2 | 10/2007 | Bi |
| 7,388,972 B2 | 6/2008 | Kitson |
| 7,394,946 B2 | 7/2008 | Dewaele |
| 7,547,307 B2 | 6/2009 | Carson |
| RE40,914 E | 9/2009 | Taylor |
| 7,837,621 B2 | 11/2010 | Krause |
| 8,055,487 B2 | 11/2011 | James |
| 8,157,800 B2 | 4/2012 | Vvedensky |
| 8,257,353 B2 | 9/2012 | Wong |
| 8,296,094 B2 | 10/2012 | Harrison |
| 8,333,766 B2 | 12/2012 | Edelhauser |
| 8,419,732 B2 | 4/2013 | Mullaney |
| 8,439,914 B2 | 5/2013 | Ross |
| 8,654,150 B2 | 2/2014 | Haskell |
| 8,731,885 B2 | 5/2014 | Iannotti |
| 8,777,946 B2 | 7/2014 | Lindahl |
| 8,864,750 B2 | 10/2014 | Ross |
| 8,945,128 B2 | 2/2015 | Singh |
| 8,952,986 B2 | 2/2015 | Haskell |
| 9,204,937 B2 | 12/2015 | Edelhauser |
| 9,895,167 B2 | 2/2018 | Edelhauser |
| 9,936,975 B2 | 4/2018 | Siemer |
| 10,010,346 B2 * | 7/2018 | Edelhauser ............ A61B 17/62 |
| 11,083,495 B2 * | 8/2021 | Edelhauser ............ A61B 34/10 |
| 11,771,466 B2 * | 10/2023 | Edelhauser ............ A61B 34/10 606/56 |
| 2002/0010465 A1 | 1/2002 | Koo |
| 2003/0191466 A1 | 10/2003 | Austin |
| 2004/0039259 A1 | 2/2004 | Krause |
| 2004/0068187 A1 | 4/2004 | Krause |
| 2004/0073211 A1 | 4/2004 | Austin |
| 2004/0073212 A1 | 4/2004 | Kim |
| 2005/0054917 A1 | 3/2005 | Kitson |
| 2005/0215997 A1 | 9/2005 | Austin |
| 2006/0276786 A1 | 12/2006 | Brinker |
| 2008/0234554 A1 | 9/2008 | Vvedensky |
| 2008/0319448 A1 | 12/2008 | Lavallee |
| 2009/0177198 A1 | 7/2009 | Theodoros |
| 2010/0087819 A1 | 4/2010 | Mullaney |
| 2010/0286995 A1 | 11/2010 | Pekar |
| 2010/0305568 A1 | 12/2010 | Ross |
| 2011/0004199 A1 | 1/2011 | Ross |
| 2011/0103556 A1 | 5/2011 | Carn |
| 2011/0103676 A1 | 5/2011 | Mullaney |
| 2011/0116041 A1 | 5/2011 | Hartung |
| 2011/0313418 A1 | 12/2011 | Nikonovas |
| 2012/0130687 A1 | 5/2012 | Otto |
| 2012/0330312 A1 * | 12/2012 | Burgherr ............... A61B 17/66 606/54 |
| 2013/0121612 A1 | 5/2013 | Falco, Jr. |
| 2014/0236153 A1 | 8/2014 | Edelhauser |
| 2015/0216564 A1 | 8/2015 | Salomone |
| 2016/0045225 A1 | 2/2016 | Edelhauser |

FOREIGN PATENT DOCUMENTS

| | | |
|---|---|---|
| RU | 2471447 C1 | 1/2013 |
| RU | 2489106 C2 | 8/2013 |
| WO | 2010104567 A1 | 9/2010 |

OTHER PUBLICATIONS

European Patent Office (ISA), International Search Report and Written Opinion dated Jun. 25, 2013 for International Application No. PCT/US2013/024548, International filing date Feb. 3, 2013.
Extended European Seach Report for Application No. 14154820.6 dated Jun. 16, 2014.
IMED Surgical, Adam Frame with Paley's Method, Workshop, Oct. 2010.
Litos GmbH, "Ilizarov Hexapod System," available from http:// d3llyibkg2zj6z.cloudfront.net/ImagemAnexo/Ilozarov-Hexapod-System.-PDF, dated May 23, 2007.
Smart Correction, Computer-Assisted Circular External Fixator System, website printout, Feb. 2, 2011.
Vreden Russian Research Institute of Traumatology and Orthopedics Ortho-SUV Ltd., Deformity Correction and Fracture Treatment by Software-based Ortho-SUV Frame, Saint-Petersburg, 2013.

\* cited by examiner

RING HOLE PLANNING FOR EXTERNAL FIXATION FRAMES

CROSS-REFERENCE TO RELATED APPLICATIONS

This application is a continuation of U.S. patent application Ser. No. 17/383,585, filed Jul. 23, 2021, which is a continuation of U.S. Pat. No. 11,083,495, filed Apr. 9, 2018, which is a continuation of U.S. Pat. No. 10,010,346, filed Apr. 20, 2016, the disclosures of which are hereby incorporated by reference herein.

BACKGROUND OF THE DISCLOSURE

Many different types of bone deformities can be corrected using external fixation systems to perform the distraction osteogenesis process. For example, an Ilizarov device or similar external fixation system may be used. Such systems generally use rings, also designated as fixation plates, connected to one another by threaded rods or struts. Each ring is coupled to the bone of interest at opposite ends of a deformity. The lengths of the struts are adjusted over time to change the position and orientation of the two rings with respect to one another, which in turn repositions and reorients the bone fragments, with a goal of correcting the bone deformity.

Each strut is attached to a position, usually a hole or other aperture, on each of the rings at the beginning of the correction procedure. As the strut lengths are changed and the correction procedure continues, the mounting locations between the struts and the frames generally remain constant. The initial mounting locations of the struts to the rings may limit the maximum range of motion between the rings, and thus limit the ability to correct certain severe deformations. However, external fixation rings systems generally include default mounting locations for the struts. The ability to mount struts to positions on the rings other than the default positions may be limited. For example, mounting struts to positions on the rings other than the default positions may lead to relatively large strut angles that reduce the stability of the fixation frame construct.

BRIEF SUMMARY

According to one aspect of the disclosure, an external fixation system including a first fixation member having a first plurality of mounting holes each configured to receive a first end of one of a plurality of struts and a second fixation member having a second plurality of mounting holes each configured to receive a second end of one of the plurality of struts. Each strut has a default mounting position corresponding to one of the holes in each of the first and second fixation members. A method of establishing mounting positions of a plurality of struts in an external fixation system includes performing a first simulation of a correction of a bone deformity with the first and second ends of the plurality of struts coupled to the first and second fixation members in the default mounting position. A second simulation of a correction of a bone deformity is performed with the first end of one of the plurality of struts coupled to the first fixation member in a first alternative mounting position, wherein in the first alternative mounting position the first end of the one strut is located in a hole different from the default mounting position. It may then be determined whether the correction of the bone deformity is achievable based on the first and second simulations. The first end and second end of each of the plurality of struts may be mounted to the first and second fixation members in the default mounting position.

It may then be determined that the correction of the bone deformity is not achievable based on the first simulation. One of the plurality of struts may be identified as a problem strut resulting in the correction of the bone deformity being not achievable. In the first alternative mounting position in the second simulation, the first end of the problem strut may be coupled to the first fixation member at one of the mounting holes directly adjacent the default mounting position in a first direction. A third simulation of the correction of the bone deformity may be performed wherein the first end of the problem strut is coupled to the first fixation member at one of the mounting holes directly adjacent the default mounting position in a second direction opposite the first direction in a second alternative mounting position. It may be determined that the correction of the bone deformity is not achievable based on the second and third simulations; and a problem strut constraint causing the correction of the bone deformity to be unachievable may be determined. It may also be determined which of the first alternative mounting position and second alternative mounting position provides greater alleviation of the problem strut constraint.

It may be determined that the first alternative mounting position provides greater alleviation of the problem strut constraint. A fourth simulation of the correction of the bone deformity may be performed with the problem strut in a third alternative mounting position in which the first end of the problem strut is coupled to the first fixation member in a mounting hole directly adjacent the first alternative mounting position in the first direction.

It may be determined that the correction of the bone deformity is not achievable based on the fourth simulation. A fifth simulation of the correction of the bone deformity may be performed with the problem strut in a fourth alternative mounting position in which the first end of the problem strut is coupled to the first fixation member in a mounting hole directly adjacent the third alternative mounting position in the first direction.

It may be determined that the correction of the bone deformity is not achievable based on the fifth simulation. A sixth simulation of the correction of the bone deformity may be performed with the problem strut in a fifth alternative mounting position in which the second end of the problem strut is coupled to the second fixation member in a mounting hole directly adjacent the default mounting position in the second direction.

It may be determined that the correction of the bone deformity is not achievable based on the sixth simulation. A seventh simulation of the correction of the bone deformity may be performed with the problem strut in a sixth alternative mounting position in which the second end of the problem strut is coupled to the second fixation member in a mounting hole directly adjacent the fifth alternative mounting position in the second direction.

It may be determined that the correction of the bone deformity is not achievable based on the seventh simulation. An eighth simulation of the correction of the bone deformity may be performed with the problem strut in a seventh alternative mounting position in which the second end of the problem strut is coupled to the second fixation member in a mounting hole directly adjacent the sixth alternative mounting position in the second direction.

The method may include beginning to perform the correction of the bone deformity by increasing a length of at least one of the plurality of struts. The correction of the bone deformity may be continued until the one strut reaches a maximum length. The first end of the one strut may be disconnected from the default mounting position and reconnected to a hole in the first fixation member different than the default mounting position. The correction of the bone deformity may be completed.

According to another aspect of the disclosure, an external fixation system includes a first fixation member having a first plurality of mounting holes each configured to receive a first end of one of a plurality of struts and a second fixation member having a second plurality of mounting holes each configured to receive a second end of one of the plurality of struts. A method of correcting a bone deformity with the external fixation system includes fixing the first fixation member to a first bone segment and fixing the second fixation member to a second bone segment. A first end of each of the plurality of struts is coupled to one of the first plurality of mounting holes of the first fixation member and a second end of each of the plurality of struts is coupled to one of the second plurality of mounting holes in the second fixation member, each of the plurality of struts being in an initial mounting position. The correction of the bone deformity may be begun by increasing a length of at least one of the plurality of struts, with the correction being continued until the one strut reaches a maximum length. The first end of the one strut may be disconnected from the initial mounting position and reconnected to one of the first plurality of holes in the first fixation member different than the initial mounting position. The correction of the bone deformity may be completed.

A position of the first fixation member may be fixed with respect to the second fixation member prior to disconnecting the first end of the one strut from the initial mounting position. The step of fixing the position of the first fixation member with respect to the second fixation member may include clamping the first and second fixation members.

The length of the one strut may be decreased after disconnecting the first end of the one strut from the initial mounting position but before reconnecting the first end of the one strut to one of the first plurality of holes in the first fixation member different than the initial mounting position. The step of completing the correction of the bone deformity may include increasing the length of the one strut after reconnecting the first end of the one strut to one of the first plurality of holes in the first fixation member different than the initial mounting position. The second end of the one strut may remain in the initial mounting position throughout the correction of the bone deformity. The same plurality of struts may couple the first fixation member to the second fixation member during the correction of the bone deformity without introducing a new strut to the external fixation system. The first and second fixation systems may each be rings having a first inner circumferential row of holes and a second outer circumferential row of holes, the initial mounting position being respective ones of the second outer circumferential rows of holes. Holes in the first inner circumferential row may be circumferentially staggered (i.e. not radially aligned) with respect to holes in the second outer circumferential row.

DETAILED DESCRIPTION

Figure 1:
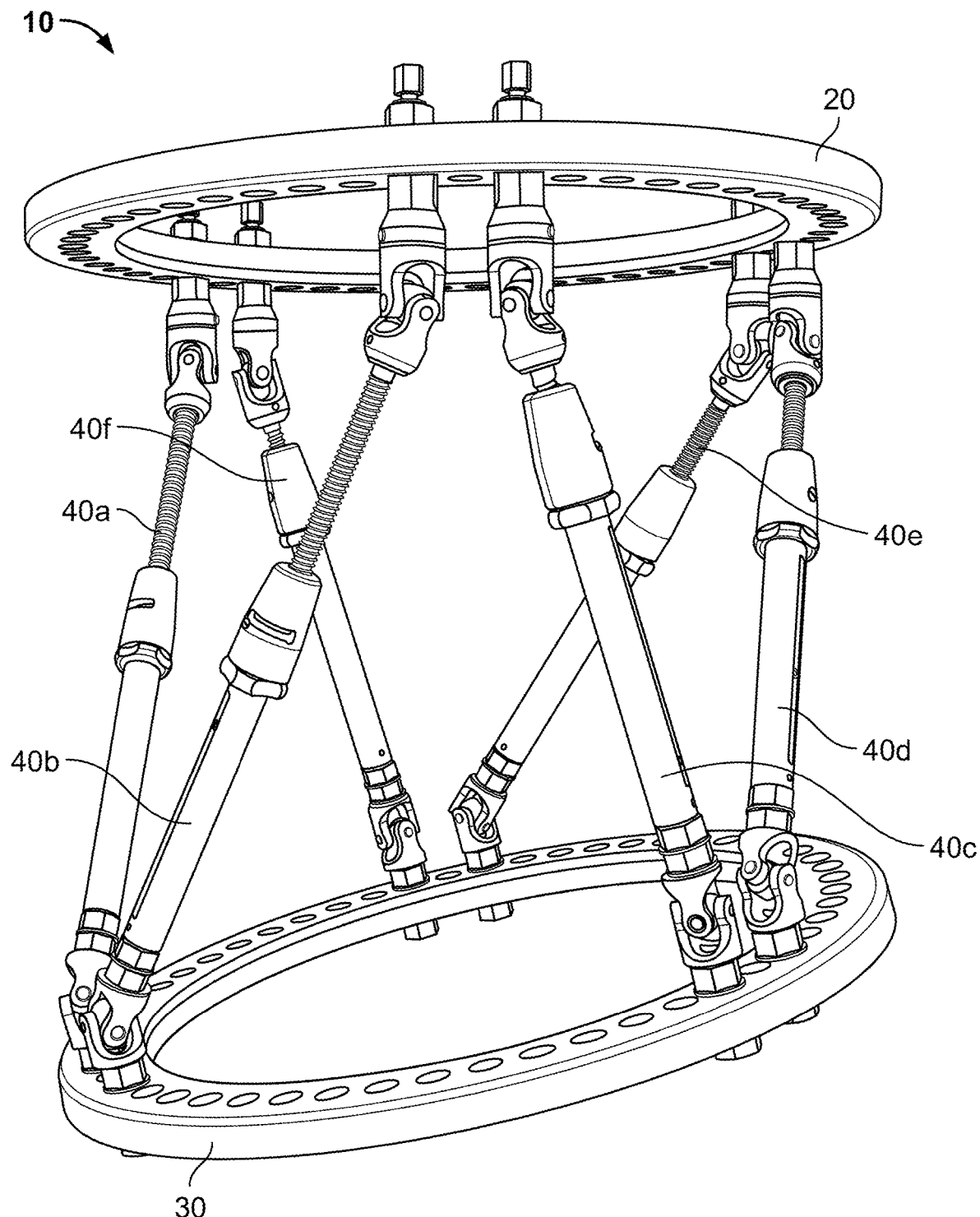
FIG. 1 is a perspective view of an external fixation frame.

FIG. 1 shows an external fixation frame 10 in an assembled condition according to one aspect of the disclosure. Generally, fixation frame 10 includes a first ring 20 and a second ring 30, with six telescopic struts 40*a-f* coupling the first ring 20 to the second ring 30. The first ring 20 may also be referred to as a proximal ring or a reference ring, while the second ring 30 may also be referred to as a distal ring or a moving ring. In the illustrated embodiment, each strut 40*a-f* includes a threaded portion that may thread into or out of a shaft portion to decrease or increase the length, respectively, of the telescopic strut. Each end of each strut 40*a-f* may be coupled to the first ring 20 and second ring 30 via a joint mechanism, such as a ball joint, a constrained hinge joint, or a universal joint as illustrated. The use of universal joints on each end of the strut provides for six degrees of freedom of motion of the external fixation system 10. Various mechanisms may be employed to adjust the lengths of the struts 40*a-f*. For example, in the illustrated embodiment each strut 40*a-f* is coupled to the first ring 20 via an actuator that extends proximally of the first ring 20. A user may engage a tool, such as a screwdriver type tool, to rotate the actuator to in turn increase or decrease the length of the particular strut 40*a-f*. It should be understood that although the disclosure is generally described in the context of closed circular rings, the concepts described herein may apply with equal force to other types of rings, such as open rings and/or U-shaped rings.

The first fixation ring 20 and second fixation ring 30 may each include a plurality of holes or apertures extending from a top surface to bottom surface of each fixation ring. For example, the first fixation ring 20 and second fixation ring 30 may each include fifty two holes spaced evenly around the circumference of the ring. In one convention, the holes are numbered from zero through fifty-one in a clockwise direction along the fixation rings 20, 30. The fixation rings 20 and 30 may include markings or other indicia adjacent certain holes in the fixation frames that correspond to desired default mounting positions for the different struts 40*a-f*. In the example of rings 120 and 130 described in greater detail below in connection with FIGS. 6A-B, the default mounting positions may be the centermost holes in the outer circumferential row 170 of each extension tab 150 (see FIG. 6B).

In some circumstances, it may be desirable to attach struts 40*a-f* to the first and second fixation frames 20, 30 at mounting locations different than the default mounting positions. In one example, there may be other components of the external fixation system 10 that would interfere with the position of the struts 40a-f. Such components could include K-wires, mounting posts, bone pins, or any other feature attached to either the first ring 20 or second ring 30, including those coupling portions of the fixation frame 10 to the patient's bone. The position of these components may be dictated by the particular surgical situation and there may be little leeway to shift the position of these components, so it may be preferable or necessary to reposition the mounting position of the struts 40a-f to avoid interference with those other components. Besides potential interference with components of fixation system 10, the struts 40a-f may also interfere with soft or hard tissue of the patient if the default mounting positions are used.

Figure 2:
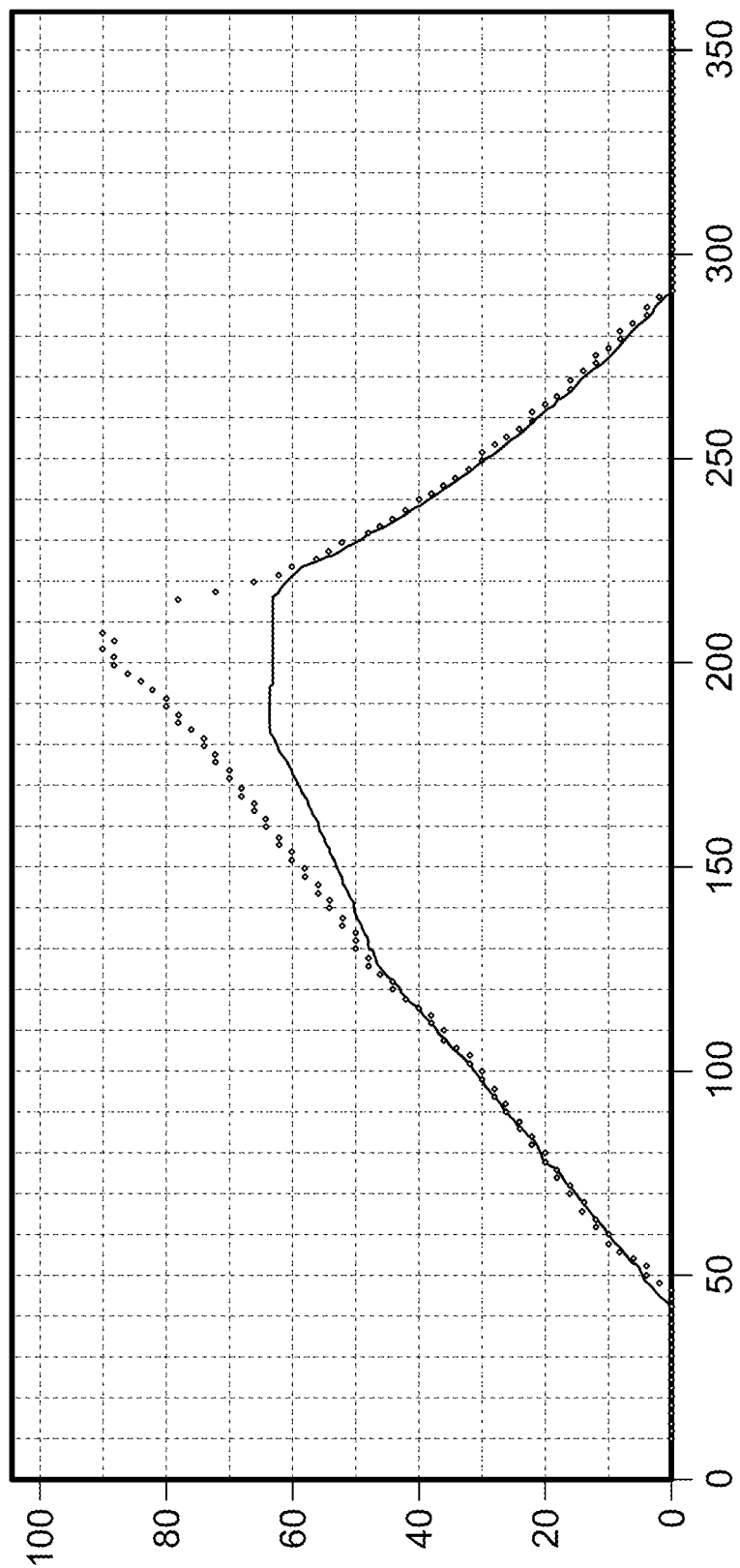
FIG. 2 is a graph showing maximum angulation of the external fixation frame of FIG. 1 for default strut mounting positions compared to certain alternate potential strut mounting positions.

In another example, in severe deformities, given a fixed range of distance between the first ring 20 and second ring 30, achieving a desired correction with struts 40a-f coupled to the first and second rings 20, 30 at the default mounting positions may be impossible. It was determined that changing the mounting positions of the struts 40a-f from the default mounting positions may increase the maximum achievable angulation. FIG. 2 illustrates a graph of maximum achievable angulation in a three strut external fixation system (provided in degrees on the y-axis) versus the distance between the top and bottom rings of the fixation system (provided in millimeters on the x-axis). In FIG. 2, the solid line represents an external fixation system in which struts are attached at default positions, whereas the dotted line represents the same system in which the struts may have their initial mounting position shifted up to three holes in the clockwise or counterclockwise direction. As can be seen in FIG. 2, it was found that the fixation frame can achieve a significantly greater degree of angulation when the struts are allowed to have an initial mounting position shifted up to three holes in the clockwise or counterclockwise direction from the default position.

Figure 3:
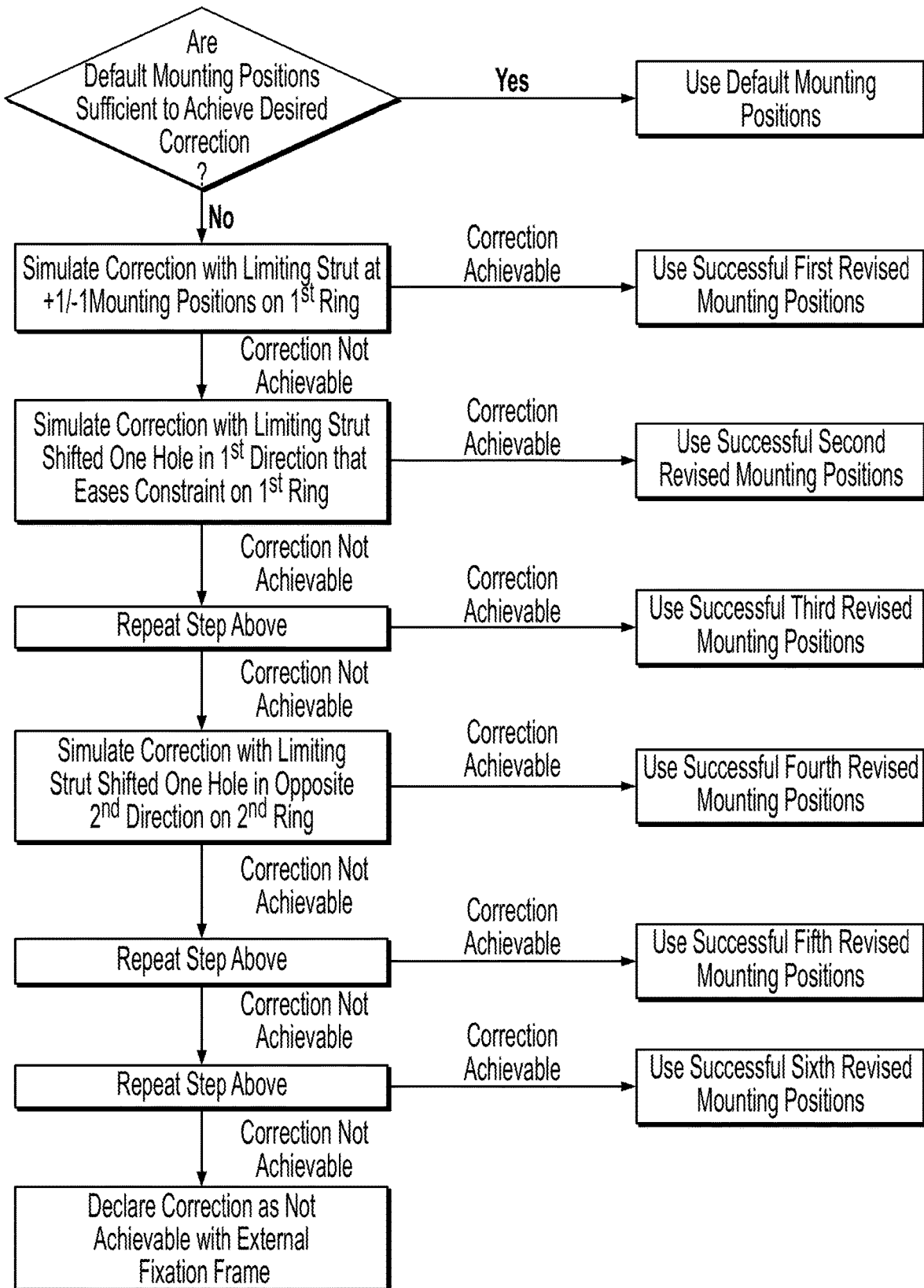
FIG. 3 is a flow chart of a method according to an aspect of the disclosure.

A series of method steps may be implemented to determine the optimum location of mounting locations for struts to the fixation frame rings. The below steps are one example for a system with three struts, similar or identical to any of struts 40a-f, and at least two fixation rings, similar or identical to rings 20 and 30. However, it should be understood that the method may also be used with other systems, including the six strut external fixation systems 10 and 110 of FIGS. 1 and 6A, respectively. For a three-strut system for use with rings 20 and 30 having fifty-two holes each, the default mounting locations for the three struts may be set as 0, 16, and 36 for each ring with the numbering being provided in a clockwise direction, beginning with 0 and ending in 51. For example, a first strut may have a default mounting position of hole 0 on both the first and second rings 20, 30, a second strut may have a default mounting position of hole 16 on the first and second rings 20, 30, and a third strut may have a default mounting position of hole 36 on the first and second rings 20, 30. In a first step, as shown in FIG. 3, a determination is made whether the three-strut system mounted at the default holes (0, 16, and 36 of each ring) is sufficient to achieve the desired correction. Such a determination may be made using planning software known in the art which is capable of simulating the desired correction using virtual fixation components corresponding to the actual fixation components and a virtual bone model corresponding to the patient's actual bone. If the desired correction may be achieved with this configuration, the default mounting positions should be used. If the desired correction cannot be achieved, the strut restricting the ability for the system to achieve the desired correction is determined, for example as an output of the software. The default mounting positions may be particular to the particular external fixation frame. For example, and as noted above, for the fixation system 110 shown in FIGS. 6A-B and described in greater detail below, the default mounting positions may be the center two holes in the outer circumferential row 170 of each extension tab 150 for each ring 120, 130.

Still referring to FIG. 3, the correction is then simulated two more times with the strut causing the limitation being in an initial mounting position on the first ring 20 shifted by one hole in the clockwise direction ([1, 16, 36] for the top ring 20) and shifted one hole in the counterclockwise direction ([51, 16, 36] for the top ring 20). If either of the two revised initial mounting positions provides the ability to achieve the desired correction, the revised initial mounting position should be used to perform the correction. If neither of the two revised initial mounting positions provide the ability to achieve the desired correction, it should be determined which of the simulated revised positions eases the constraint causing the problem. For example, if the first strut is limiting the ability to achieve the desired correction because the strut angle is too extreme at some point in the correction process, and the modified mounting position of +1 (at hole 1) causes the angle to increase in extremity and the modified mounting position of −1 (at hole 51) causes the angle to decrease in extremity, another correction simulation should be performed with the initial mounting position modified another hole in the direction that eases the constraint, in this case in the negative or counterclockwise direction. In other words, at this point another simulation would be performed with the initial mounting position of the first strut at [2, 16, 36] for the top ring 20. If the correction is achievable with this mounting position, it should be used to achieve the correction. If the relevant constraint is still violated, the simulation is performed one more time with the problematic strut shifted one more hole in the same direction, which in this example would be at [3, 16, 36] for the top ring 20. Again, if the correction is achievable in this third revised position, the third revised position should be used to achieve the correction. However, if shifting the strut three holes in the first ring 20 (either in the clockwise or counterclockwise direction depending on which direction eases the constraint) does not allow the correction to be achieved, the mounting position of the strut is moved in the opposite direction one hole on the second or bottom ring 30, and the correction is simulated again. In this example, if the mounting position [3, 16, 36] for the top ring 20 and [0, 16, 36] for the bottom ring 30 still does not allow the desired correction to be achieved, the mounting position of the first strut on the bottom ring 30 is moved in the opposite direction one hole to [51, 16, 36] and the correction is simulated again. This process is repeated until a suitable mounting position is found that allows the correction to be achieved, or otherwise until a maximum of three position shifts have been attempted on the first ring in the first direction and three position shifts have been attempted for the same strut on the second ring in the second opposite direction. If three position shifts for the problem strut are simulated on each ring, in this case to a maximum of [3, 16, 36] for the top ring 20 and [49, 16, 36] for the bottom ring, and the correction is still not able to be achieved, a determination is made that the correction cannot be achieved using the external fixation frame. It should be understood that although the method above is described in terms of first changing the mounting positions of the top ring 20 and then subsequently changing the mounting positions of the bottom ring 30, this order does not need to be strictly followed. However, changing the mounting position of strut on the top ring 20 generally leads to a more prominent angle change than a corresponding mounting position change in the bottom ring 30, so it is preferable to attempt first, second, and third mounting position shifts, if necessary, in the top ring 20 before beginning to change the mounting positions of a strut to the bottom ring 30. Although the constraint is generally described herein as strut angle or length constraints, other relevant constraints include a strut causing undesirable visibility or if the strut is in the way of other fixation frame components, such as points of wire fixation or apex pins of the system.

Figure 4A:
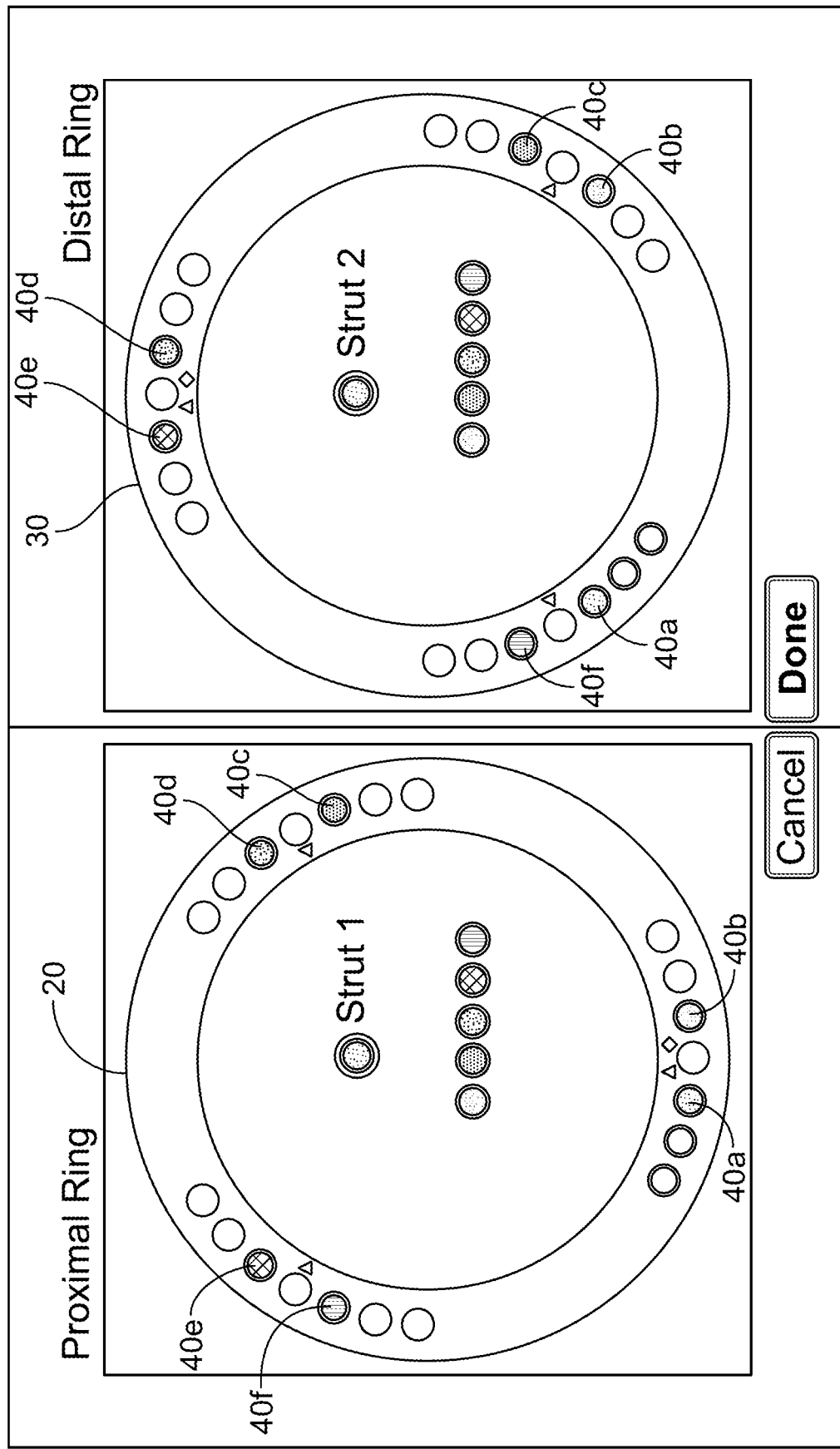
FIG. 4A is an example of a display image showing struts in default positions in according with an aspect of the disclosure.

In order to assist a surgeon in carrying out the above process, it is preferable that the surgeon is provided with an intuitive software interface to assist in the determinations. For example, the surgeon may be provided with a display operatively connected to a computer system with one or more associated processors and memories, with the software being stored on one of the associated memories and with the operation of the software assisted by one or more of the associated processors. FIG. 4A illustrates an image that may be displayed by the software on a display accessible to the surgeon, the image including a top view of the proximal or top ring 20 of the external fixation system 10 of FIG. 1 and a top view of the distal ring or bottom ring 30 of the external fixation system 10 of FIG. 1. The images of top ring 20 and bottom ring 30 may indicate default mounting positions of struts 40a-f by providing an indicator within the particular hole of the ring that the strut is intended to be mounted in the default position. For example, the default mounting position of each strut 40a-f may be indicated by a color filling the corresponding default mounting hole within the image of the hole provided on the display, with each strut corresponding to a unique color. As can be seen in FIG. 4A, other indicia may be provided on the image of the top and bottom rings 20, 30 to indicate default mounting positions. For example, shapes such as triangles or rectangles may be provided directly on the rings 20, 30 to indicate where the default mounting positions are. It should be understood that similar or identical indicia may be printed or otherwise provided on the physical rings themselves. In the illustrated example, triangle shapes are provided adjacent particular holes on the top and bottom ring 20, 30. For a six strut system, the triangle shapes indicate that the default position of one strut is on a first side of the indicator and the default position of another strut is on the other side of the indicator, with a total of three indicators on each rings indicating the default mounting position of six struts in all. For a three strut system, the triangles correspond directly to the default hole mounting positions. Other indicators, such as the square indicator shown, may indicate a four strut system.

With the struts 40a-f displayed on top ring 20 and bottom ring 30 in default positions, a user may click or otherwise select a particular strut on the display, and upon selecting that strut, additional possible mounting positions of the strut may be illustrated or otherwise indicated. For example, in FIG. 4A, the first strut 40a is shown in its default position, with the two holes immediately adjacent the first strut 40a default hole in the counterclockwise direction (as viewed from above) highlighted as potential alternate positions. Similarly, for the first strut 40a in the second or bottom ring 30, two strut holes immediately adjacent the first strut 40a default hole in the clockwise direction (as viewed form above) are highlighted as potential alternate positions. Upon performing a simulation of the correction, if the default positions of struts 40a-f allow for the correction to be achieved, the default positions may be used for the correction. It should be understood that the number of maximum hole offsets may depend on the particular fixation system, but generally a maximum number of hole offsets of two or three may be suitable.

Figure 4B:
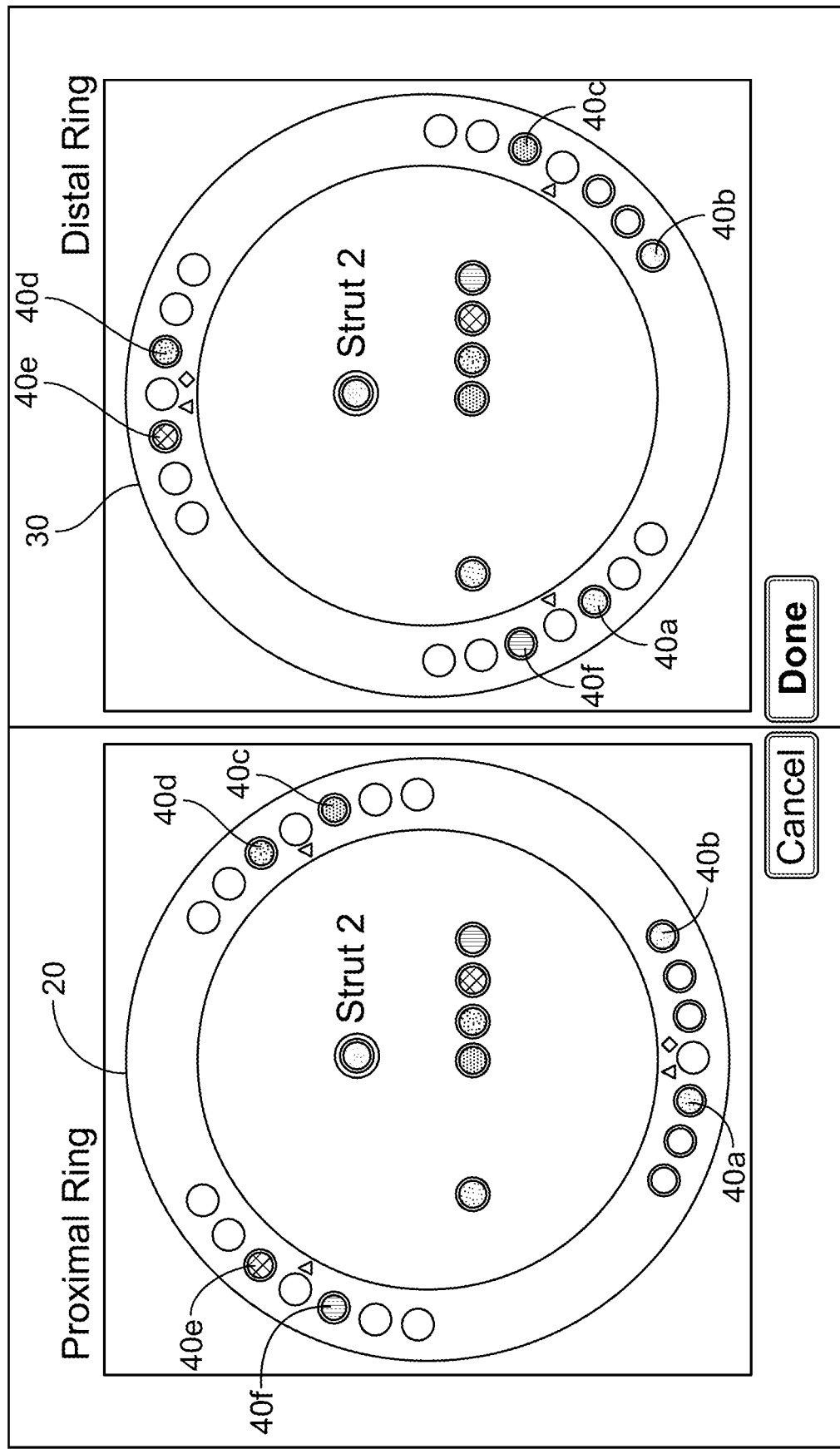
FIG. 4B is an example of a display image showing struts in default positions with at least one strut in a non-default position.

FIG. 4B illustrates the displayed image in FIG. 4A after it was determined that the fixation system 10 could not achieve the desired correction with the second strut 40b in the default position. As shown in FIG. 4B, the user, after selecting the second strut 40b, potential alternate mounting holes for second strut 40b were highlighted or otherwise indicated to the user. By selecting the desired revised mounting hole for second strut 40b, for example by clicking the desired hole among the alternate options presented, the mounting position of the second strut 40b changes. In FIG. 4B, the mounting position of the second strut 40b in the top ring 20 was shifted two holes in the counterclockwise direction, with the mounting position of the second strut 40b in the bottom ring 30 shifted two holes in the clockwise direction.

Figure 4C:
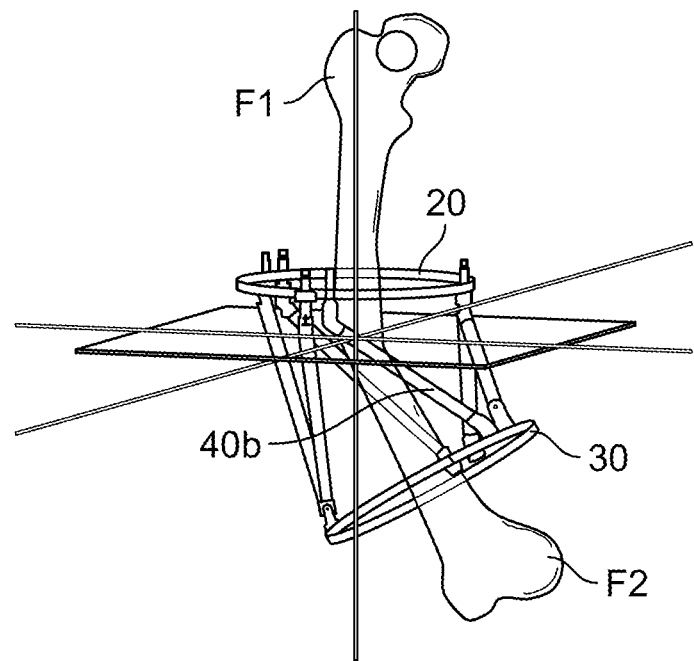
FIG. 4C illustrates a display of an external fixation system with the strut configurations of FIG. 4A.
Figure 4D:
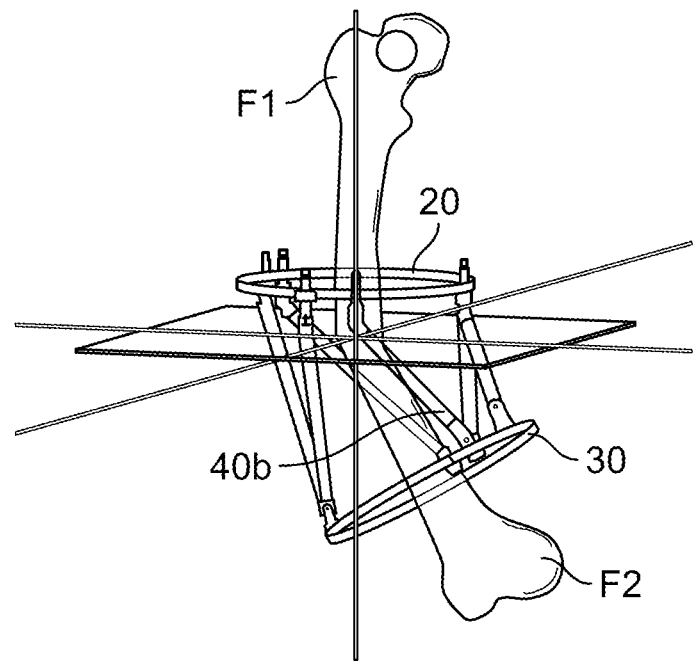
FIG. 4D illustrates a display of an external fixation system with the strut configuration of FIG. 4B.

The software may also update a model of the fixation system 10 each time the user shifts the mounting hole(s) of a strut 40a-f to provide the surgeon a view of the fixation system 10. For example, FIG. 4C illustrates a perspective view of fixation frame 10 with top ring 20 coupled to a first bone fragment F1 and bottom ring 30 coupled to a second bone fragment F2, with struts 40a-f in their default mounting positions of FIG. 4A. After the user changes the mounting positions of second strut 40b from the default positions two holes counterclockwise in the top ring 20 and two holes clockwise in the bottom ring 30, as shown in FIG. 4B, the display of the fixation frame may update, as shown in FIG. 4D, to show the user what the fixation frame 10 would look like with the updated strut positions. This may help the user confirm, for example, that a strut such as strut 40b has a more stable angle in the updated fixation frame 10 configuration of FIG. 4D compared to the default fixation frame 10 configuration of FIG. 4C.

Another potential issue that arises during the course of correction of a bone using fixation frame 10 is the potential necessity of a strut change-out. As noted above, during the correction process, one or more of the telescopic struts 40a-f are increased in effective length by threading the threaded rod portion of the strut out of the shaft to move a first end of the strut away from the opposite end of the strut, effectively increasing the effective length of the strut. Struts often come in standard sizes, such as small struts, medium struts, and large struts, the struts being generally classified by a maximum achievable effective length. During the correction procedure, a particular telescopic strut may be extended to its maximum effective length (or alternatively shortened to its minimum effective length), prior to completing the correction procedure. In a case where a telescopic strut reaches its maximum effective length prior to finishing the correction procedure, the patient often needs to go the appropriate medical personnel to have the strut replaced with a larger strut capable of a greater effective length than the strut that reached its maximum effective length. In order to complete this procedure, the first frame 20 and second frame 30 must generally be fixed in position with respect to one another and the bone, for example using a clamp system to attach to both rings 20 and 30 and to constrain the system in every degree of freedom so that up to five of the six struts may be removed without altering the position and orientation of the rings. The strut at its maximum effective length is removed from the fixation frame 10, and the new larger strut is coupled to the fixation frame in the same mounting positions as the removed strut. It should be understood that although the method described herein is provided relative to eliminating the need for a strut change-out to a larger strut after a strut reaches its maximum effective length, the concepts would apply to eliminating the need for a strut change-out to a smaller strut after a strut reaches a minimum effective length.

Figure 5A:
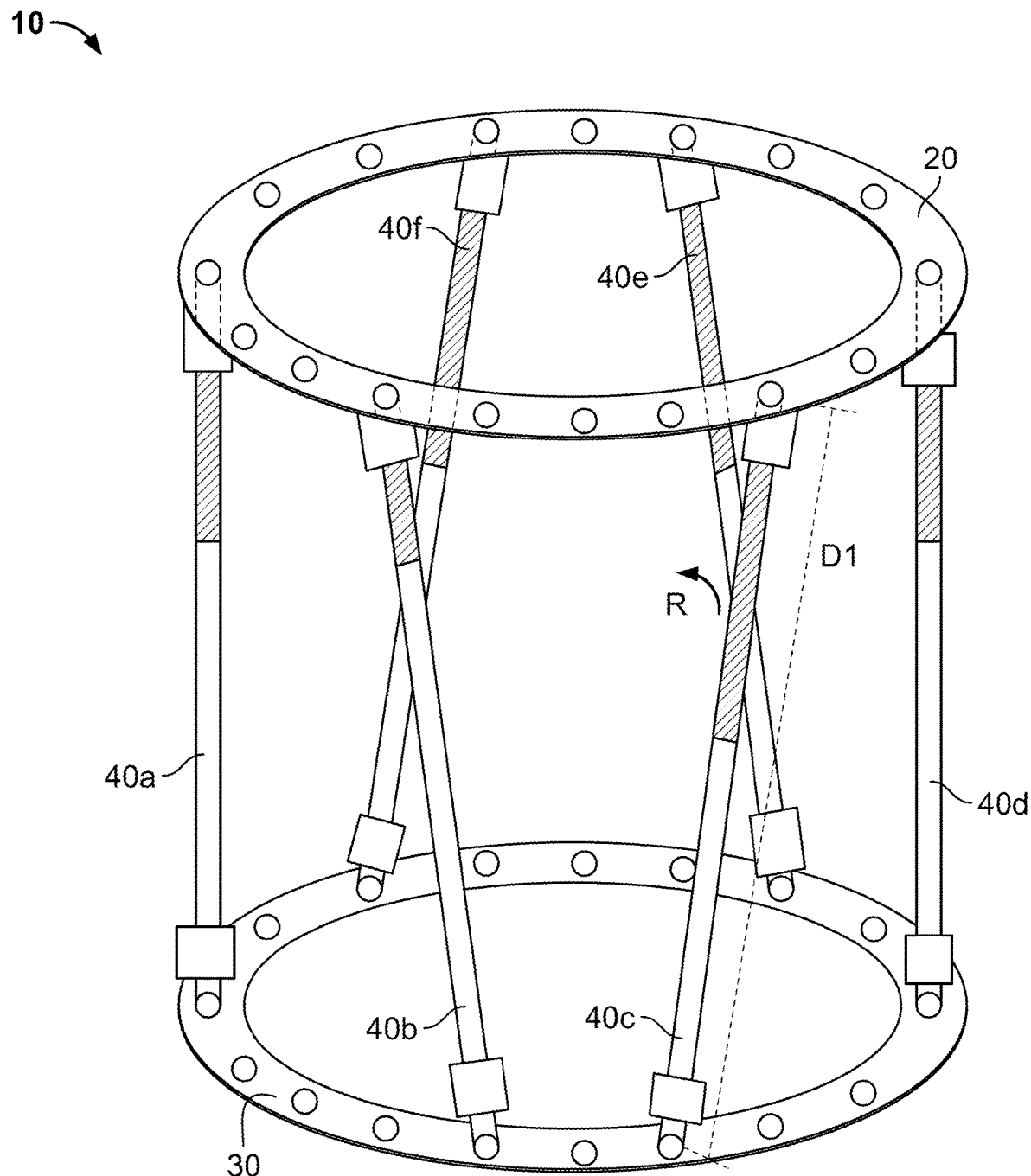
FIG. 5A is a schematic view of the external fixation frame of FIG. 1 with one strut at a maximum length.
Figure 5B:
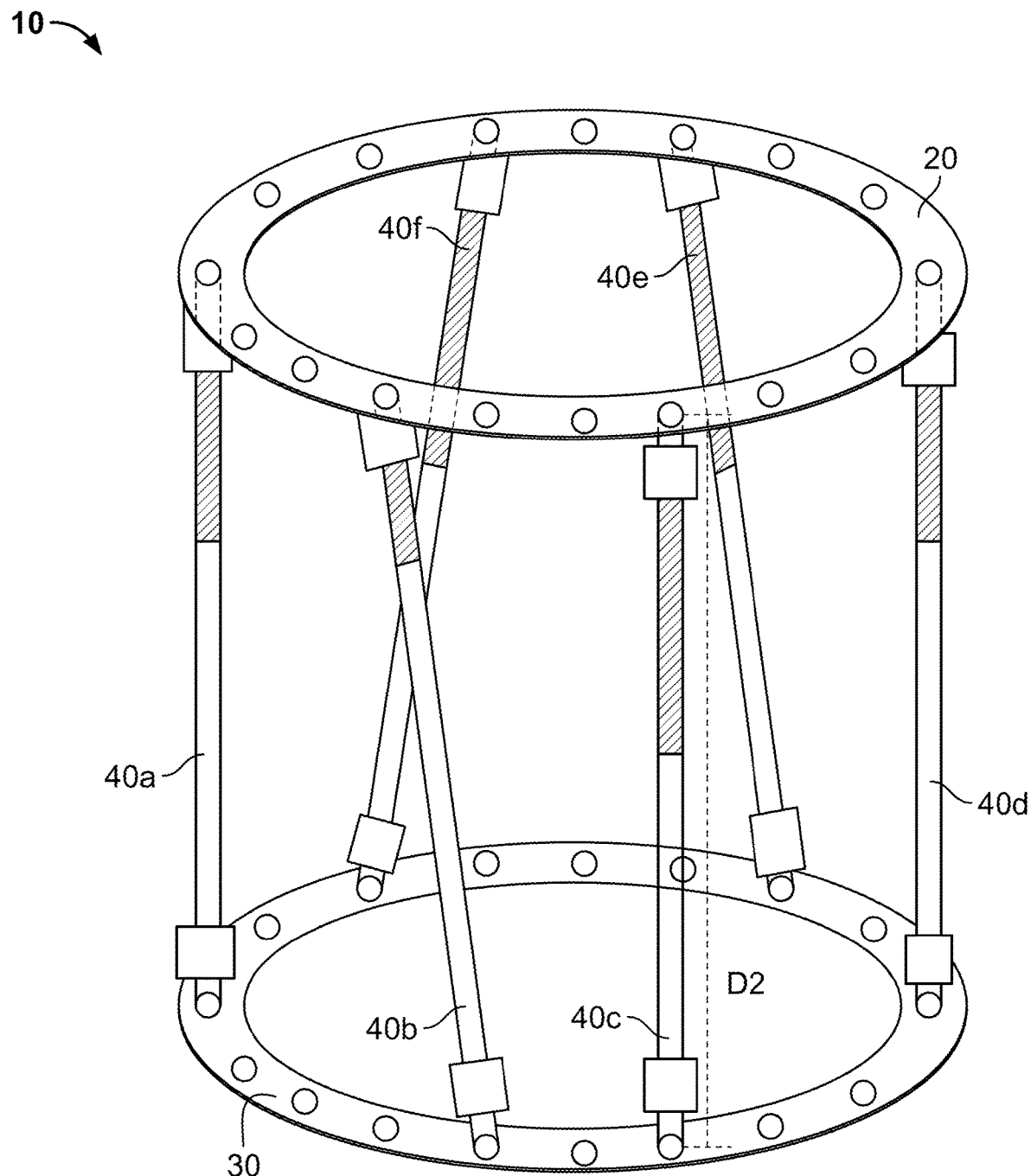
FIG. 5B is a schematic view of the external fixation frame of FIG. 5A after repositioning one of the struts.

As should be understood, the requirement of one or more additional struts to complete the correction procedure may increase the complexity and particularly the overall cost of the procedure. As an alternative to changing out a strut after the strut reaches its maximum effective length, the mounting position of the strut may be changed with respect to one or both fixation rings using the same strut. If the distance between the new mounting holes is less than the distance between the current mounting positions where the strut is at its maximum effective length, the new mounting position will provide the ability for the strut to further increase in length so that the correction may be completed. This ability is provided by the new angle between the strut and the fixation rings. FIGS. 5A-B illustrate the above method, but it should be understood that the components of external fixation system 10 are not necessarily provided to scale.

In FIG. 5A, fixation frame 10 is shown with six struts 40a-f coupling the top ring 20 to the bottom ring 30, with strut 40c having been increased in length to its maximum possible effective length. It should be understood that generally, rings 20 and 30 would not be parallel at this point in the correction, but are shown to be parallel merely for simplicity. Strut 40c is coupled to a first hold on the top ring 20 and a second hole on the bottom ring 30, with a distance of $D_1$ being between the respective holes. If the correction called for a further increase in length of strut 40c, the correction would not be able to be completed with strut 40c remaining in the position shown in FIG. 5A. Traditionally, strut 40c would be replaced with a larger strut connecting to the same holes that strut 40c is shown connected to in FIG. 5A. However, to avoid the need to use another strut, another solution is to connect strut 40c to different holes on the top ring 20 and/or bottom ring 30 to allow strut 40c to continue to cause movement of rings and 30 with respect to one another. Because strut 40c is at its maximum effective length when coupled to holes in the top ring 20 and bottom ring 30 having a distance $D_1$, the strut 40c may be connected to a different hole in the top ring 20, a different hole in the bottom ring 30, or both, so long as the new hole positions are at a distance from one another less than $D_1$. In other words, as long as the angle of the strut 40c between the first ring 20 and second ring 30 transitions closer to being perpendicular the top ring 20, the strut 40c will be able to provide for additional correction.

As shown in FIG. 5A, strut 40c may be kept fixed to the original mounting hole in the bottom ring 30, with the strut 40c rotated in the direction R so that the top of strut 40c connects to a new mounting hole. To accomplish this, rings 20 and 30 would be clamped with respect to one another by medical personnel and strut 40c detached from at least the top ring 20. Strut 40c would then need to be shortened a degree because the distance between the new mounting holes $D_2$, as shown in FIG. 5B, is less than the original distance $D_1$ between the original mounting holes. With the clamps keeping rings 20 and 30 fixed in their original position, and with the strut 40c shortened from its maximum effective length, the medical personnel couple the top of strut 40c to the new mounting hole in top ring 20. Because strut 40c needed to be shortened to make the new connection between rings 20 and 30, it becomes available to continue lengthening via the telescopic action described above to further reposition ring 20 with respect to ring 30. Once the clamps are removed, the correction may continue. It should be understood that although a single strut 40c is illustrated as having only one of its mounting hole positions changed, one or more struts 40a-f may have their positions change to avoid the requirement of adding new struts to the system, and the new position may be only a new mounting hole in the top ring 20, only a new mounting hole in the bottom ring 30, or new mounting hole positions for both the top and bottom rings 20, 30. Assuming a strut 40a-f reaches its maximum effective length prior to the correction procedure being completed, the only requirements for changing strut position are that (a) the distance between the new hole mounting positions is less than the distance between the previous hole mounting positions, and (b) the correction is achievable with the strut in the new mounting positions. If the method is being used to reposition a strut after it has reached its minimum effective length, the distance between the new hole mounting positions must be greater than the distance between the previous hole mounting positions.

Figure 6A:
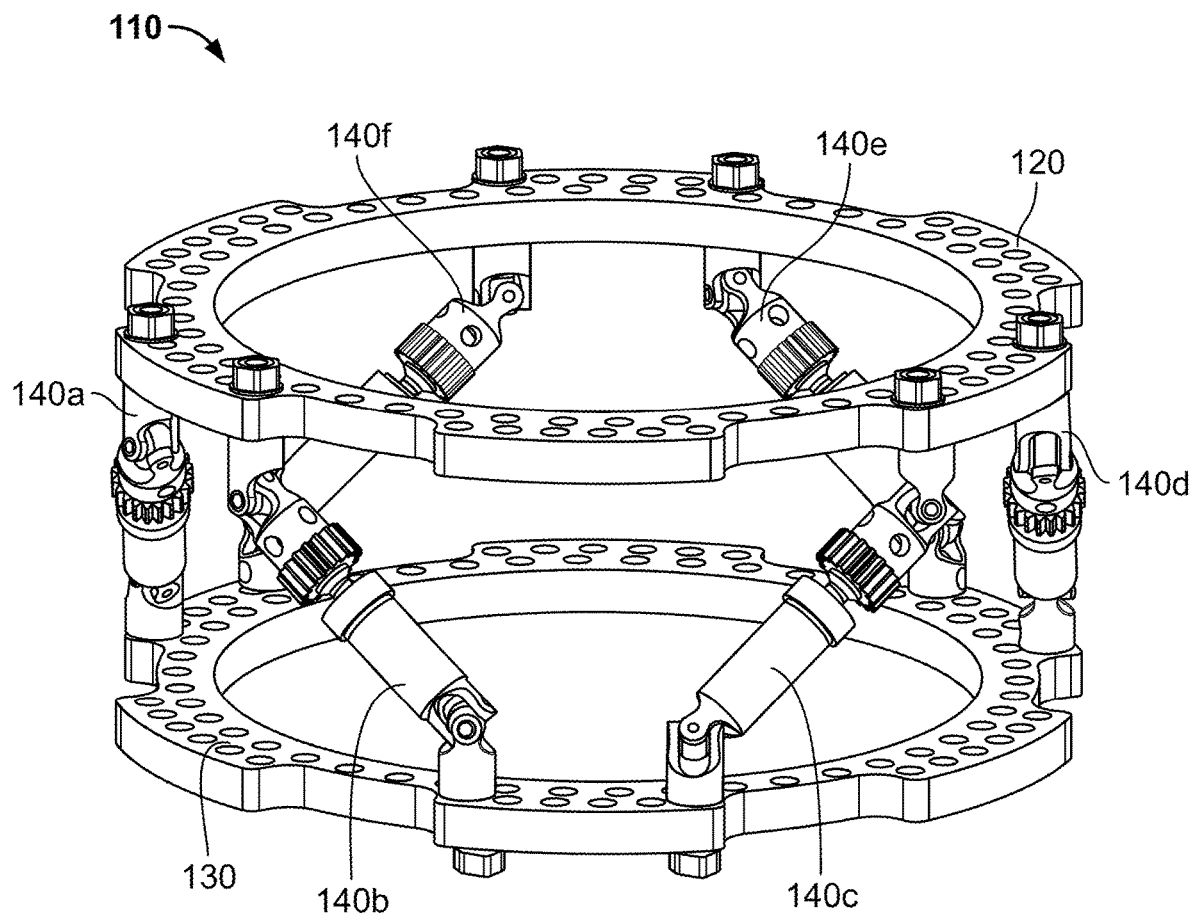
FIG. 6A is a perspective side view of an external fixation frame according to another aspect of the disclosure.
Figure 6B:
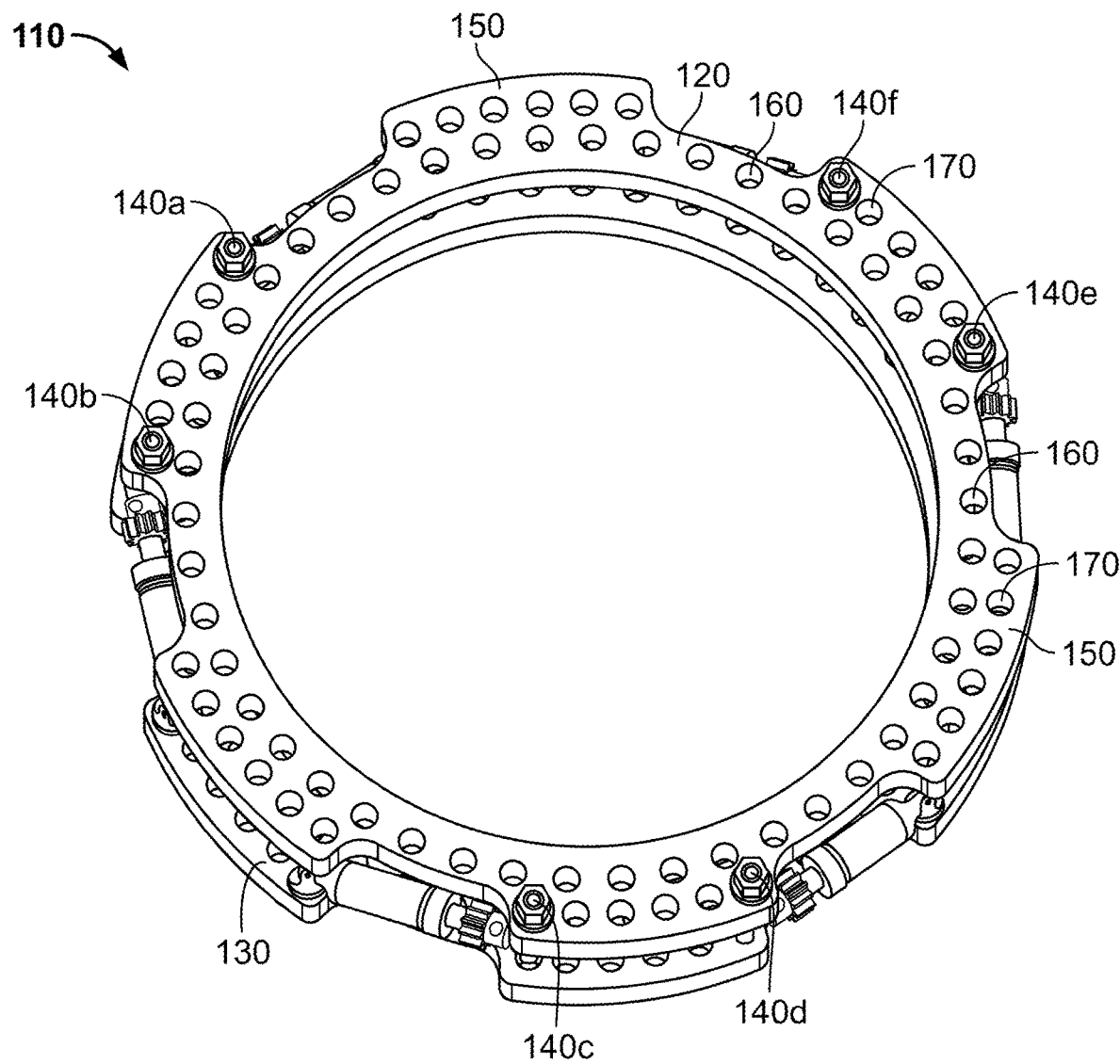
FIG. 6B is a perspective top view of the external fixation frame of FIG. 6A.

The concepts described above may be applied to other fixation systems with other types of rings. For example, FIGS. 6A-B illustrate an external fixation system 110 according to an aspect of the disclosure. External fixation system 110 is generally similar to external fixation system 10 with certain difference. External fixation system 110 includes a top ring 120 and a bottom ring 130 coupled to one another by a plurality of telescopically extending struts 140a-140f similar to external fixation system 10, However, unlike rings 10 and 20, rings 120 and 130 include a plurality of extension tabs 150, as best seen in FIG. 6B. In the illustrated example, each ring 120 and 130 includes six extension tabs 150 spaced circumferentially around the perimeter of the respective rings, although more or fewer may be suitable depending on the particular components of the fixation system. In addition to what is described directly below, extension tabs 150 may help increase the cross-sectional area of rings 120, 130 and thus provide for increased stiffness of the rings.

With this configuration, each ring 120, 130 includes a first inner circumferential row of holes 160 and a second outer circumferential row of holes 170. As illustrated, the second outer circumferential row of holes 170 may be only positioned on the plurality of extension tabs 150 on the rings 120 and 130. It should be understood that although the second outer circumferential row of holes 170 is shown in FIGS. 6A-B as being positioned solely on extension tabs 150, top ring 120 and/or bottom ring 130 may contain two complete rows of holes, for example with a completely circular (or nearly completely circular) geometry. The use of extension tabs 150, compared to two full circumferential rows of holes, may help reduce overall bulk of rings 120, 130 and also provide for intuitive strut placement for surgical personnel. The completely circular version of rings 120, 130 with two full (or nearly full) rows of circumferential holes may be particularly suited for relatively small diameter rings, although indentations or other features may be introduced to provide an intuitive interface for strut placement by surgical personnel. Further, in the illustrated embodiment, the first and second circumferential rows of holes 160 and 170 are positioned so that the first row of holes 160 does not align radially with the second row of holes 170. In other words, the first row of holes 160 has a staggered configuration with respect to the second row of holes 170. With struts 140a-f initially coupled to holes in the second circumferential row 170 on extension tabs 150 in the top and bottom rings 120 and 130, the correction may proceed until it is complete or until one or more of the struts 140a-f reaches its maximum effective length. Similar to the description above in connection with FIGS. 5A-B, the rings 120 and 130 may be clamped or otherwise fixed if one or more struts 140a-f reach their maximum effective lengths, and whichever strut(s) 140a-f is at a maximum length may be disconnected from one or both rings 120, 130, and recoupled to another hole or holes to increase the maximum effective length of the strut. The strut 140a-f at its maximum length may be coupled to circumferentially adjacent hole 170 at a less acute angle similar to described in connection with FIGS. 5A-B. Alternatively, the strut 140a-f at its maximum length may be connected to a hole in the first circumferential row 160 of the top and/or bottom rings 120, 130. The presence of two rows of circumferential holes 160 and 170 in a staggered configuration may provide more options for reconnecting a particular strut 140a-f to effectively increase the range of length of the strut while being able to maintain the planned trajectory of the rings 120 and 130 during the deformity correction process. The additional hole options may also be utilized for connecting other components, such as fixation pins to couple the rings 120, 130 to the respective bone fragments. Still further, the staggered configuration of holes between the first and second rows 160, 170 may also help prevent interference between components attached to nearby holes, for example such as a strut positioned in a first hole and a fixation pin or other fixation member attached to an adjacent or nearby second hole. For example, a relatively thin wire extending radially from one of the holes in the first circumferential row 160 may not radially interfere with a hole positioned in the second circumferential row 170 because of the radial staggering. It should be understood that the size of the tabs 150 may increase or decrease depending on the diameter of the rings 120 and 130, with greater diameter rings 120 and 130 having larger tabs 150 with more holes 170 compared to smaller diameter rings. For example, the illustrated tabs 150 include six holes 170, and a smaller ring may include smaller tabs with four holes each, for example. Regardless of the size of the particular ring and corresponding tab, the stagger pattern of the holes in the first and second circumferential rows may be maintained. In addition to the benefits described above, the concepts provided herein may allow for less complex struts compared to an external fixation system that uses more expensive and complex struts, for example a double telescoping strut system, to solve the problem of strut change-outs when a strut reaches its maximum effective length.

Finally, it should be understood that the concepts and methods described above regarding the choice of initial mounting positions for struts in an external fixator system may be used with or without the concepts and methods described in relation to changing the mounting position of one or more struts during the progression of the correction itself. Similarly, the concepts and methods described in relation to changing the positions of one or more struts mid-correction may be used with or without the concepts described above regarding the choice of initial mounting positions for the struts.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A method of ring hole planning for an external fixation frame, the method comprising:
    displaying on a display device a first virtual fixation ring including a plurality of virtual holes, the first virtual fixation ring corresponding to a first physical fixation ring, the plurality of virtual holes corresponding to a plurality of physical holes in the first physical fixation ring;
    displaying on the display device a first portion of a virtual strut positioned within a first one of the virtual holes in a virtual default strut mounting position, wherein the virtual strut corresponds to a physical strut;
    the first virtual hole corresponding to a first one of the physical holes, the first physical fixation ring including an indicator adjacent to the first physical hole to indicate the first physical hole is a physical default strut mounting position;
    determining that a desired correction cannot be performed with the physical strut mounted to the first physical fixation ring at the physical default strut mounting position;
    in response to determining that the desired correction cannot be performed, selecting on the display device, via a user input device, a second one of the virtual holes, wherein the second virtual hole corresponds to a second physical hole of the first physical fixation ring, the second physical hole being a physical non-default strut mounting position;
    in response to selecting the second virtual hole, updating the display device to display the first portion of the virtual strut positioned within the second virtual hole; and
    determining that the desired correction can be performed with the physical strut mounted to the first physical fixation ring at the physical non-default strut mounting position.

2. The method of claim 1, wherein the first virtual hole is directly adjacent to the second virtual hole.

3. The method of claim 1, wherein the physical non-default strut mounting position is a first physical non-default strut mounting position, and wherein a third virtual hole is positioned between the first virtual hole and the second virtual hole, the third virtual hole corresponding to a third physical hole of the first physical ring, the third physical hole being a second physical non-default strut mounting position.

4. The method of claim 1, further comprising, in response to determining that the desired correction can be performed, mounting the physical strut to the first physical fixation ring at the physical non-default strut mounting position.

5. The method of claim 1, further comprising, after determining that the desired correction cannot be performed, highlighting on the display device all valid virtual non-default strut mounting positions that correspond to the virtual default strut mounting position.

6. The method of claim 1, wherein the first virtual fixation ring is a proximal virtual fixation ring, and the first portion of the virtual strut is a proximal portion of the virtual strut.

7. The method of claim 6, further comprising:
    displaying on the display device a virtual distal fixation ring including a plurality of virtual distal holes extending through the virtual distal fixation ring.

8. The method of claim 7, wherein the distal virtual fixation ring corresponds to a second physical fixation ring, the second physical fixation ring being a distal physical fixation ring, the first physical fixation ring being a proximal physical fixation ring.

9. The method of claim 8, wherein the plurality of virtual distal holes correspond to a plurality of physical distal holes in the distal physical fixation ring.

10. The method of claim 9, further comprising:
displaying on the display device a virtual representation of a distal portion of the strut positioned within a first one of the virtual distal holes.

11. The method of claim 10, wherein the first virtual distal hole corresponds to a first one of the physical distal holes, the distal physical fixation ring including a second indicator adjacent to the first physical distal hole to indicate the first physical distal hole is a physical default distal strut mounting position.

12. The method of claim 11, further comprising, in response to determining that the desired correction can be performed, mounting the physical strut to the proximal physical fixation ring at the physical non-default strut mounting position, and mounting the physical strut to the distal fixation ring at the physical default distal strut mounting position.

13. The method of claim 12, further comprising coupling fix additional physical struts to the proximal physical fixation ring and to the physical distal fixation ring so that at total of six physical struts connect the proximal physical fixation ring to the physical distal fixation ring.

14. The method of claim 13, wherein the physical proximal fixation ring includes a first group of physical holes that are aligned in a first circumferential row.

15. The method of claim 14, wherein the physical proximal fixation ring includes a plurality of tabs extending radially outward of the first circumferential row.

16. The method of claim 15, wherein the physical proximal fixation ring includes a second group of physical holes that are aligned in a second circumferential row positioned within the plurality of tabs.

17. The method of claim 1, wherein the first virtual fixation ring is a distal virtual fixation ring, and the first portion of the virtual strut is a distal portion of the virtual strut.

18. The method of claim 17, further comprising:
displaying on the display device a virtual proximal fixation ring including a plurality of virtual proximal holes extending through the virtual proximal fixation ring.

19. The method of claim 18, wherein the proximal virtual fixation ring corresponds to a second physical fixation ring, the second physical fixation ring being a proximal physical fixation ring, the first physical fixation ring being a distal physical fixation ring.

20. The method of claim 19, wherein the plurality of virtual proximal holes correspond to a plurality of physical proximal holes in the proximal physical fixation ring.

\* \* \* \* \*